United States Patent [19]

Voorhies et al.

[11] Patent Number: 4,784,150
[45] Date of Patent: Nov. 15, 1988

[54] SURGICAL RETRACTOR AND BLOOD FLOW MONITOR

[75] Inventors: Rand M. Voorhies, New Orleans, La.; Craig M. Housworth, Oklahoma City, Okla.; Antonio J. Waring, New Orleans, La.

[73] Assignee: Research Corporation, New York, N.Y.

[21] Appl. No.: 927,209

[22] Filed: Nov. 4, 1986

[51] Int. Cl.⁴ .......................... A61B 5/02; A61B 17/02
[52] U.S. Cl. .................................. 128/664; 128/691; 128/20
[58] Field of Search ...................... 128/3, 20, 664–666, 128/691, 748

[56] References Cited

U.S. PATENT DOCUMENTS

| | | |
|---|---|---|
| 3,605,726 | 9/1971 | Williams et al. ............... 128/691 |
| 3,769,974 | 11/1973 | Smart et al. .................. 128/666 |
| 4,263,900 | 4/1981 | Nicholson ..................... 128/20 |
| 4,414,980 | 11/1983 | Mott .......................... 128/664 |
| 4,597,030 | 6/1986 | Brody et al. .................. 128/20 X |
| 4,619,249 | 10/1986 | Landry ........................ 128/20 X |

FOREIGN PATENT DOCUMENTS

| | | | |
|---|---|---|---|
| 2570266 | 3/1986 | France ................ | 128/20 |
| 2133694 | 8/1984 | United Kingdom ...... | 128/20 |

Primary Examiner—Edward M. Coven
Assistant Examiner—Angela D. Sykes
Attorney, Agent, or Firm—Scully, Scott, Murphy & Presser

[57] ABSTRACT

A surgical retractor instrument which incorporates therein a blood flow monitor. A surgical retractor system is disclosed for manipulation of living tissues and/or organs during diagnostic and/or surgical procedures, providing for the monitoring of the presence or absence of blood flow in the tissue adjacent thereto. The surgical retractor incorporates a surgical retractor blade, which can be of any conventional or desired design or physical shape, depending upon the intended use thereof. The pressure end of the retractor blade is designed with fiber optics for directing light (specifically IR) having predetermined spectral characteristics related to blood onto the adjacent tissues and/or organs. The retractor blade is also designed with receiving fiber optics for receiving light which is directed at and reflected from the tissues and/or organs. A signal processor is coupled to the light receiving optics for monitoring the signal received therefrom to direct the presence or absence of blood flow through the adjacent tissues and/or organs, thereby preventing and minimizing ischemic damage therein.

7 Claims, 11 Drawing Sheets

FIG. 12 CORRELATION OF CEREBRAL PULSATIONS, BLOOD PRESSURE, AND ECG SIGNALS.

FIG. 13 DECREASE OF CEREBRAL PULSATION AMPLITUDE WITH INCREASING PRESSURE (PAGE 1 OF 2)

SURGICAL RETRACTOR AND BLOOD FLOW MONITOR

BACKGROUND OF THE INVENTION

1. Field of the Invention

The present invention relates generally to a surgical retractor which incorporates therein a blood flow monitor, and more particularly pertains to a neurological surgical retractor which monitors for the pressure of cerebral blood flow in the tissue adjacent to the retractor to prevent and minimize ischemic damage therein.

2. Discussion of the Prior Art

A variety of debilitating cerebral pathologies can now be treated by surgical procedures. Intracranial aneurysms, angiomas and certain types of tumors are among the many conditions which are surgically correctable. Often, a surgical instrument known as a retractor is used to give additional exposure of tissue in the operating field. Microsurgical techniques, which require extensive use of the light microscope, often require a version of the retractor known as the "Yasargil" or "self-retaining" retractor, while in other situations, a "hand-held" retractor is employed.

While use of these retractors, often for several hours, is necessary to expose the surgical site, surgeons and particularly neurosurgeons have worried that the pressure exerted on the delicate neurologic tissues can cause damage thereto. The neurosurgeon has traditionally relied on his experience and "feel" in setting a safe level of retractor pressure. This may prevent physical crushing or mechanical damage of the tissues, but of greater concern is the possibility of severely compromised local blood flow under the retractor head. This reduced blood flow could lead to oxygen starvation of the tissue cells called cerebral ischemia. This type of damage cannot be visually detected by the surgeon, even with the use of a microscope.

Cerebral blood flow may already be reduced during these surgical procedures due to a loss of autoregulation of the brain, cerebral edema, a mass lesion, induced hypotension, or fluctuations in arterial $pCO_2$. This necessitates even more restraint in the use of excessive retractor pressures.

While damage due to retractor pressure has been suspected for many years, controlled studies to isolate this effect have appeared only recently. Numoto and Donaghy (1970) investigated the correlation between local pressure and electroencephalogram (EEG) changes. They concluded that "cortical electrical activity is suppressed as a result of changes in local blood flow which are in turn a result of local compression and tissue distortion."

Other EEG parameters have been shown to correlate with cerebral ischemia and could prove useful in evaluating or predicting damage caused by retractor pressure. Tolonen and Sulg (1981) found that the power in the delta band (0.0 to 4.69 Hz) of the EEG power spectrum correlated inversely with regional cerebral blood flow, such that an increase of EEG power in this band could warn of impending ischemic damage. Pronk and Simons (1982) concluded that the Hjorth time domain parameter of "mobility" (Hjorth, 1970) was sensitive to cerebral ischemia. Mobility is defined as the square root of the ratio between the variances of the EEG signal first derivative and the EEG amplitude. The ratio indicates average slope of the signal, and its square root, which is the standard deviation of the power spectrum along the frequency axis, indicates mean EEG frequency.

Rosenorn and Diemer (1983) applied various lead weights to the cortical surfaces of rats for fifteen or thirty minutes. Regional cerebral blood flow was determined by means of autoradiography with carbon-14 iodoantipyrine. Radiographic densitometry was determined by computerized image analysis. Blood flow immediately beneath the retractor was found to be dramatically lower than in surrounding regions (Table I). Others (Astrup et. al., 1981) have found that flow rates below 10 to 13 ml/100 gm/min lead to cell damage. Here, pressures as low as 20 mmHg for thirty minutes caused reduction of blood flow to 10–75 ml/100 gm/min and, presumably, ischemic damage.

Albin and co-workers (1975) attached a microcircuit strain gage to a retractor blade to measure applied pressure. A self-retaining retractor was applied for one hour, then released, and Evan's Blue dye was injected intravenously. Lack of blood brain barrier integrity was evaluated the extent of staining in brain sections. This procedure was repeated at five different pressure levels. Severe blood barrier compromise was found at pressures above 20 mmHg.

In a subsequent study (1977), Albin and co-workers compared somatosensory evoked potential amplitude with the pressure gradient (cerebral perfusion pressure minus brain retractor pressure), and found a direct relationship between these two factors. Pressures above only 10 mmHg were found to cause somatosensory evoked potential changes during induced hypotension. Induced hypotension is often used in neurosurgery to minimize the risk of an aneurysm rupture. These results showed that the pressure gradient was an effective predictor of brain damage, since a certain minimum level of cerebral perfusion pressure gradient assured adequate local blood flow. This parameter effectively compensated for variations in perfusion pressure, since the retractor pressure was continually adjusted to yield a constant pressure gradient.

Yokoh and co-workers (1981) investigated cerebral tissue damage in dogs using continuous and intermittent retraction. Evans' Blue staining and electroencephalogram power spectral arrays were examined after one hour of retraction. Six different pressure levels were used, and at each level, two groups of experiments were performed. The first group underwent continuous retraction for one hour. The second group was administered six cycles of retraction, each cycle consisting of ten minutes of retraction at the same level as the first group and five minutes of total release from pressure between cycles of retraction. Applied pressure was monitored with a strain gage apparatus attached to the self-retaining retractor.

Both power spectral arrays and morphologic studies showed marked superiority of the intermittent procedure over the continuous technique at each pressure level. The electroencephalogram power spectral array showed distinct recovery during each release phase of the intermittent retraction. The authors assumed that this finding was due to blood flow recovery under the retractor during release. They found that "the brain tolerates on average about 70% more intermittent retraction than continuous retraction from a morphological standpoint while electrophysiologically the difference is about 40%."

The "pressure" values reported by Yokoh cannot be directly compared with other studies because of the unfortunate choice of units. The values reported are in grams, a unit of mass of force, not pressure. A weight of certain mass was hung from the retractor tip before each experiment, the observed deflection was noted. A subsequent pressure level which caused an identical deflection would be reported as being pressure "equal" to the mass of the calibration weight. From the physical description the retractor used, the actual surface ar contact with the brain was probably around 120 mm². Using this to convert Yokoh's gram values to units of pressure, the upper limit to pressure without damage in the continuous case was found to be 19 mmHg. In the intermittent case, it was found to be 30 mmHg.

Donaghy et. al. (1972) took the idea of retractor pressure monitoring one step farther. They developed an inflatable bladder which could be slipped over the end of a normal brain retractor blade. A pressure switch inside the bladder monitored applied pressure and acted as the feedback loop for an infusion-withdrawal pump connected to the bladder. Thus, if retractor pressure was too high, the pressure switch would close, causing withdrawal of air from the bladder and decreasing the applied pressure. If the retractor pressure was below the setpoint, air would be infused and more tissue would be exposed. The pressure setpoint could be maintained within about 5 mm of water limits with the device. Donaghy found electroencephalogram changes with pressures exceeding 250 mm of water (18.4 mmHg).

Rather than monitor absolute applied pressure or pressure gradient, Carter and co-workers (1978 and 1982) used a Peltier stack thermal diffusion probe placed on the cortical surface to more directly measure local blood flow. This device was calibrated by comparison with Xenon washout curves, and gave a quantitative output in units of ml/100 gm/min. The probe immediately detected compromised local blood flow which resulted when excess retractor pressure was applied.

Rosenon and Diemer (1983) showed that blood flow in the deeper areas of the brain (basal ganglia) was unaffected by retractor pressure which caused flow cessation in the surface cortical tissue. In addition, cortical grey matter requires four times more blood flow than the deeper white matter (Dripps, et al, 1982).

An indirect indicator of blood flow in tissue is the presence or absence of arterial and capillary bed pulsations which occur with each heartbeat. One method commonly used for detecting these pulsations is infrared densitometry. The infrared region of the electromagnetic spectrum extends from 690 nanometers to 300 micrometers in wavelength. As an increased volume of blood is forced into the capillary bed with each pulse pressure wave, the transmission of infrared light through the tissue is altered. This technique does not measure the flow of blood in a readily quantifiable way, but instead merely detects the peaks of the signals to measure the pulse rate. It should be noted, however, that such a system is known to evaluate the absence of appreciable blood flow. "Pulse watches" based on this technical approach are ineffective when capillary bed perfusion is reduced, such as when jogging in cold weather with unprotected hands. In such commercial devices, the fingertip or ear lobe is inserted into a light-tight enclosure or clip containing an infrared source and detector. The detector continuosly measures the amount of reflected or transmitted infrared light. A level detector circuit counts the reflection peaks for a defined period of time (usually a few seconds), then converts this count to a pulse rate (beats/minute). Such circuits have been incorporated into "pulse watches" for athletes, aerobic training participants, and hypochondriacs. In some of these devices, a finger clip is wired to the watch, or the finger is placed over the infrared emitter/detector area on the watch face when a pulse rate is desired.

Another related area of the prior art concerns oximeters for measuring the saturation of hemoglobin with oxygen in the blood. In a typical oximeter, two different infrared wavelengths of radiation are monitored, a first reference wavelength which is substantially unaffected by the saturation of hemoglobin with oxygen, and a second measurement wavelength which is very sensitive to the saturation of hemoglobin with oxygen. The signals obtained at the two different wavelengths of infrared radiation are then compared to determine the saturation of hemoglobin with oxygen in the blood. These prior art oximeters, however are not designed to, and do not measure the quantitative flow of blood.

Moreover, some existing experimental retractor designs use strain gages mounted on the retractor to measure the applied retraction force. While this is a step in the right direction, the damage caused by excessive retractor pressure is mostly a result of tissue ischemia secondary to reduced or obliterated blood flow in the tissue, and is not mechanical damage caused by the physical crushing of the tissue. The amount of retractor pressure needed to obliterate blood flow is not constant, but varies widely depending on anesthetic depth, systemic blood pressure, brain pathology, location of retraction, etc.

In summary, none of the prior art discussed hereinabove provides a surgical instrument provided with an effective contruction designed specifically to monitor blood flow in the tissue adjacent to the retractor to minimize and prevent ischemic damage therein.

SUMMARY OF THE INVENTION

Accordingly, it is a primary object of the present invention to provide a surgical retractor instrument which incorporates therein a blood flow monitor.

A further object of the subject invention is the provision of a surgical retractor wherein one of several different types of surgical retractors, each provided with optical apparatus for monitoring blood flow, can be used with one optical and electronic signal generating and monitoring unit.

In accordance with the teachings herein, the present invention provides a surgical retractor system for manipulation of living tissues and/or organs during diagnostic and/or surgical procedures, providing for the monitoring of the flow of blood in the tissue adjacent thereto. The surgical retractor incorporates therein a surgical retractor blade, which can be of any conventional or desired design or physical shape, depending upon the intended use thereof. The pressure end of the retractor blade is designed with optics for directing light having predetermined spectral characteristics related to blood onto the adjacent tissues and/or organs. The retractor blade is also designed with receiving optical means for receiving light which is reflected from the tissues and/or organs. A signal processor is coupled to the light receiving means for monitoring the signal received therefrom for indicating the quantitative flow of blood through the adjacent tissues and/or organs.

In greater specificity, in one disclosed embodiment the surgical retractor is a neurological surgical retractor, the light is infrared radiation selected with predetermined spectral characteristics for the detection of blood and the flow of blood in the adjacent tissues and/or organs is monitored to prevent and minimize ischemic damage therein.

The present invention by directly sensing the blood pulsations, is an adaptive system which automatically compensates for the particular physiological state of the brain. The device should be inexpensive to manufacture, easy to incorporate into existing retractor styles, and should be inobtrusive to the surgeon. The retractor is electrically isolated from the patient because of the use of fiber optic cables.

In several disclosed embodiments, the retractor blade is constructed with a light supplying optical fiber extending from a remote light source to a site end thereof at the site of the adjacent tissues and/or organs to direct light thereon. The retractor also includes a light detecting optical fiber extending from a site end thereof at the site of the adjacent tissues and/or organs, at which it receives light reflected therefrom and directs the light to a remote end thereof at which the light is detected. A remote processing unit is coupled to the remote end of the light providing optical fiber, and a light source directs light into the remote end. The remote processing unit also has a light detector coupled to the remote end of the light detecting optical fiber to detect the light reflected from the tissues and/or organs, and the remote processing unit can also provide a visual display indicating the monitored status of the flow of blood. Moreover, both remote ends of the optical fibers are preferably removably coupled to the remote processing unit, such that any one of several different retractor blades may be selectively coupled to the processing unit.

In a preferred embodiment, the light supplying optical fiber is provided with a beveled site end to reflect light supplied thereto onto the adjacent tissues and or organs through a first given solid angle, and the light detecting optical fiber is also provided with a beveled site end to reflect light received from the adjacent tissues and/or organs through a second given solid angle into the light detecting optical fiber for detection thereof. In this arrangement, the first given solid angle intersects the second given solid angle to enable light reflected from the adjacent tissues and/or organs to be detected.

BRIEF DESCRIPTION OF THE DRAWINGS

The foregoing objects and advantages of the present invention for a surgical retractor and blood flow monitor may be more readily understood by one skilled in the art with reference being had to the following detailed description of several embodiments thereof, taken in conjunction with the accompanying drawings wherein like elements are designated by identical reference numerals throughout the several views, and in which.

DETAILED DESCRIPTION OF THE DRAWINGS

Figure 1:
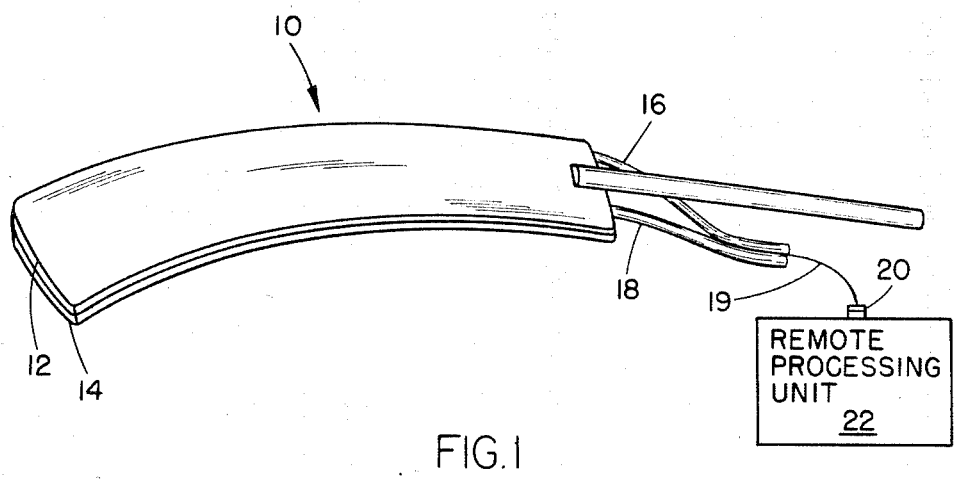
FIG. 1 illustrates a perspective view of one embodiment of a surgical retractor instrument constructed pursuant to the teachings of the present invention.
Figure 2:
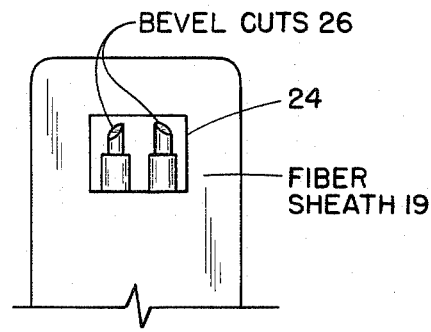
FIG. 2 is a bottom view of the pressure end of the surgical retractor instrument of FIG. 1.

Referring to the drawings in detail, FIG. 1 is a schematic illustration of a possible commercial embodiment of a surgical retractor constructed pursuant to the teachings of the present invention. In this embodiment, the surgical retractor 10 is formed by two similar adjacent flexible metal plates 12, 14 having two optical fibers, a light supplying optical fiber 16, and a light detecting optical fiber 18, positioned therebetween. The two optical fibers are shown separately for ease of explanation in FIG. 1, but in a practical embodiment would emerge from the retractor in a single protected cable 19, which plugs by a releasable coupling 20 into a remote processing unit 22.

Figure 3:
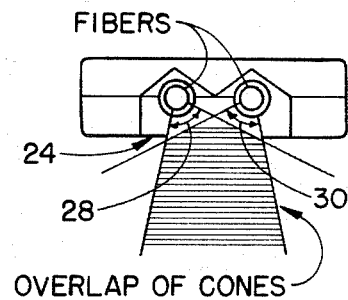
FIG. 3 illustrates an end sectional view of the surgical retractor instrument of FIG. 1, and shows the overlap of the optical cones defined by the beveled ends of the fiber optic cables therein.
Figure 4:
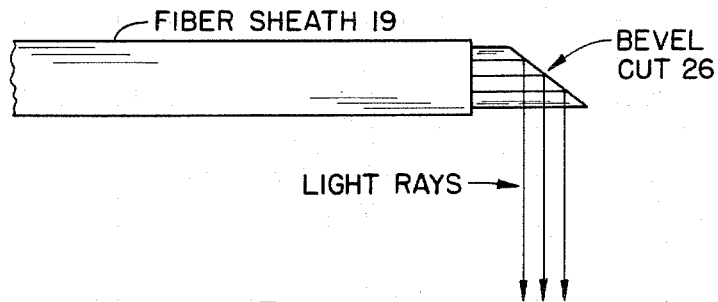
FIG. 4 illustrates how the beveled end cuts of the optical fiber cables reflect light therefrom.

An aperture 24 is cut in the pressure applying underside of the surgical retractor to allow for the emission and detection of the light, specifically IR radiation, by the two optical fibers 16, 18. A bevel cut 26 at the site end of each optical fiber allows the IR light to be reflected therefrom in a manner as shown in FIG. 4. Because of the sharp angle of each bevel cut and the great difference in the refractive indices of the optical fiber and air, the light rays are reflected off of the inner surface of the bevel cut and out through the lower side of the light supplying optical fiber 16, and in through the lower side of the light detecting optical fiber 18. Each beveled cut 26 of each optical fiber defines a solid angle cone of emission 28 or solid angle cone of acceptance 30 which intersect in a manner as illustrated in FIG. 3. This construction technique allows the site ends of the optical fibers to be properly positioned to define the intersecting cones of emission and acceptance, while maintaining the optical fibers recessed within the aperture 20 in the pressure applying end of the surgical retractor.

The optical fibers 16 and 18 leading from the surgical retractor are covered by a fiber sheath 19, and are preferably packaged in a single cable 19 which has a snap-in coupling 20 to a remote processing unit, which has an IR light source for the remote end of the optical fiber 16 and an IR light detector for the remote end of the optical fiber 18. The remote processing unit also incorporates therein all power supplies and signal processing circuits as described in greater detail hereinbelow with reference to a test embodiment. This construction is advantageous as it allows a plurality of different types of retractor blades for different surgical procedures, all constructed with light emitting and detecting fiber optics as explained hereinabove, to be utilized with one processing unit 22.

Figure 5:
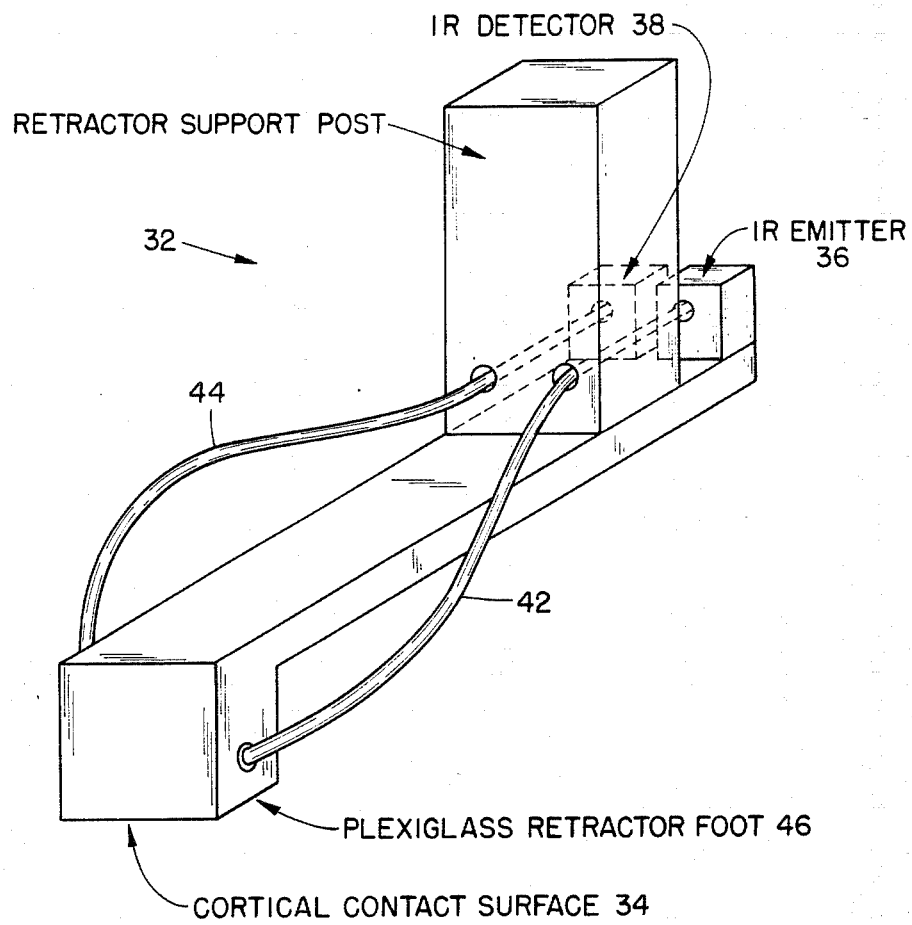
FIG. 5 illustrates a test embodiment of the present invention which was constructed to test the principles of operation thereof.

FIG. 5 illustrates a test embodiment 32 of the present invention which was contructed to enable the principles of operation of the present invention to be tested on animals. The test embodiment also incorporated thereon strain gages and EEG electrodes (both not shown) attached to the retractor to simultaneously measure local electroencephalogram and applied pressure. It should be emphasized that the test unit 32 was specifically designed for testing, and as such does not represent a commercial design for the present invention, which is better illustrated by the design of the embodiment of FIG. 1.

The test instrument 32 was used in controlled experiments to investigate the relationship between relative percentage pressure, with pressure causing total flow occlusion set to 100%, cerebral pulsations, and brain tissue damage as determined by Evans' Blue staining and electroencephalographic parameters.

The cerebral pulse detector of FIG. 5 consists of two major sections. The retractor assembly includes the retractor cortical contact surface 34, an optical infrared transmitter 36 and receiver 38, EEG electrodes (not shown), and strain gages (not shown) to sense mechanical deformation. As the retractor is pressed down, local blood flow will be occluded, and the blood pulsations measured by the detector should decrease sharply or disappear. If the infrared emitter 36 is set at a continuous output level, simple amplification and filtering provides a pulse output signal from the detector. The retractor assembly is connected to a signal processing device 40, FIG. 8, which has two functions. First, it amplifies, filters and displays the cerebral pulse signal. Secondly, it provides a convenient electrical interface connections for devices which process and display the electroencephalogram and the applied strain signal.

The model retractor itself was constructed of plexiglass to simplify fabrication and because its transparency allows for precise retractor placement on the cortical surface of the brain. Plexiglass also has a relatively low modulus of elasticity (about 3000 MPa) which yields high amplitude strain gage signals for a given applied stress.

For reasons discussed hereinabove, the infrared sensor is preferably designed to detect only reflections from vessels immediately under the retractor and close to the cortical surface. This is the region in which a dramatic pulsation decrease (and potential ischemic damage) is expected with excessive retractor pressures. To accomplish shallow reflection measurement, the emitter and detector were placed at the back of the retractor and linked optically to the cortical surface with single-step index plastic optical fibers 42, 44 (Hewlett-Packard HFBR-3510). Guide holes drilled into the plexiglass foot 46 served to hold each fiber optic at a 30 degree fixed angle to the cortical surface. The fiber optic cables were held in the holes by friction fits.

Figure 6:
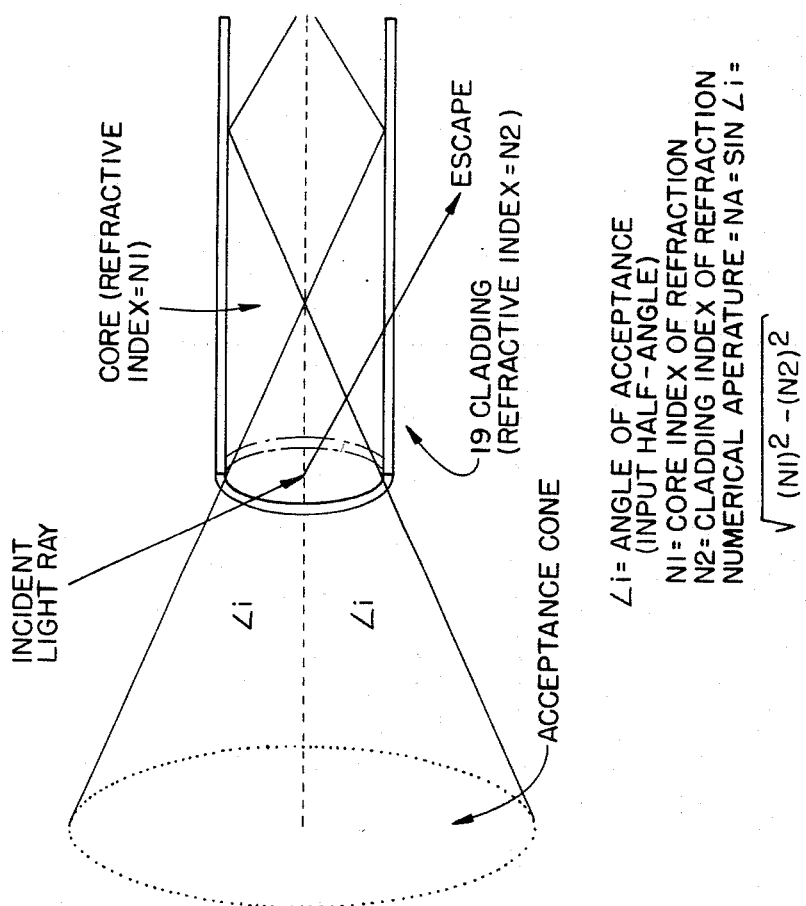
FIGS. 6 and 7 illustrate the principles of operation of the fiber optic cables in the embodiment of FIG. 5.

The entrance of light into a well-polished fiber optic end is characterized by the "numerical aperture" (NA) of the optic cable (Seippel, 1984). Numerical aperture is defined as the sine of the angle of acceptance and is determined by the refractive indices of the fiber core and its outer cladding sheath 19. Light rays must strike the fiber end at an angle less than or equal to the angle of acceptance in order to enter the fiber and be propagated. Light which strikes at a greater angle will be reflected off the end or be absorbed into the cladding (FIG. 6). The exit of light from an optic cable end is subject to the same constraints, i.e. the cone of emission is the same as the cone of acceptance.

Figure 7:
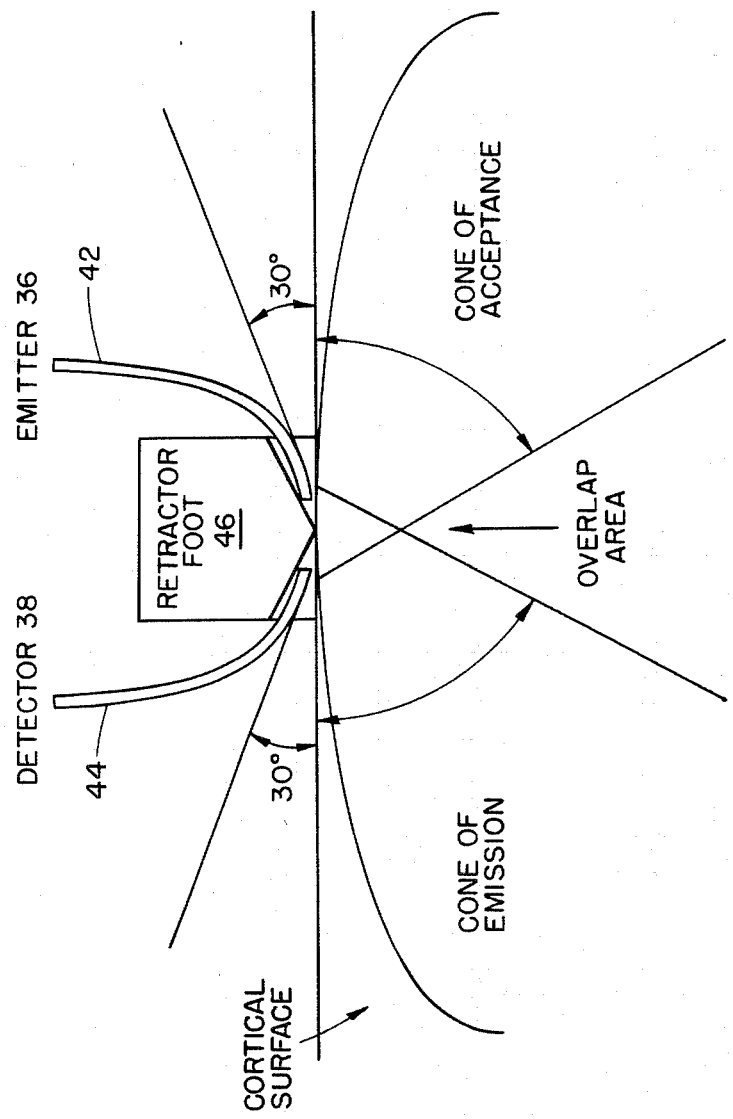

The numerical aperture for the optic cable was 0.5, which corresponds to an acceptance angle of 30 degrees. The cables themselves were each held at a 30 degree angle to the retractor contact surface. This results in a small area of overlap between the cone of emission of infrared light and the cone of acceptance of the detector cable (FIG. 7). This measurement extends to a theoretical depth of about 2 mm at the bottom point of the triangular area. This area is close to the brain's surface and is located directly below the retractor foot, which accomplishes the design goal.

It should be noted that infrared light from other sources of radiation (including incandescent and fluorescent lights) impinge upon the exposed cortical surface during neurosurgery. The contact surface of the retractor foot was painted with black enamel to prevent stray IR light from shining through the plexiglass and onto the brain surface directly below the retractor foot. However, extraneous infrared light can reflect off of distant blood vessels into the detector fiber optic. This source of infrared pulsations is not under the retractor and will not be affected by retractor pressure. Therefore, the contribution of this signal source should be excluded from the measurement of pulse amplitude. This can be accomplished incorporating a switch into the device so that the infrared emitter may be turned on and off. With the switch off, the measured pulsation amplitude will be entirely due to the extraneous IR sources. This amplitude can then be subtracted from measurements taken with the emitter on to yield a measure of pulse amplitude due to pulsations of vessels illuminated only by the emitter (and therefore taken from the area directly under the retractor).

Snap-in fiber optic link components from Hewlett Packard (Hewlett-Packard, 1984) were used to couple the fiber optic cables with the infrared emitter 26 and detector 28 components. The HP emitter module link (HFBR-1510) contained a photodiode which emitted visible light at 665 nm. This diode was removed from the plastic housing and replaced with a Radio Shack 276-142 (Radio Shack, 1986) photodiode, which has peak emission at 915 nm. In a similar fashion, the digital phototransitor receiving circuit in the receiver module (HFBR-2501) was replaced with a Radio Shack 276-142 IR analog phototransistor. The lenses of the replacement IR components were ground flat on an abrasion wheel and polished to provide good optical coupling between component and optic fiber. Use of the snap-in connectors facilitated easy removal and replacement of the short fiber optic cables.

Figure 8:
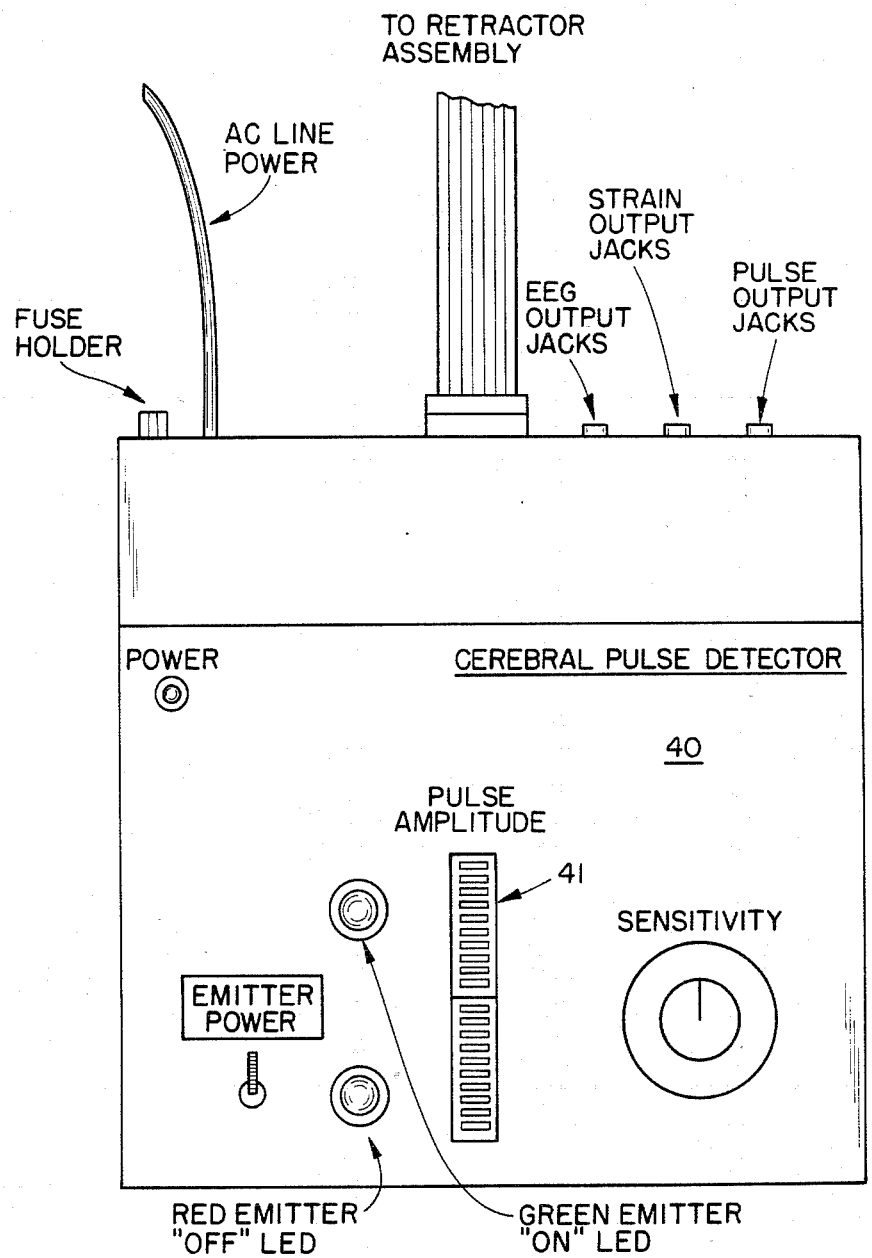
FIG. 8 is a front view of the pulse detector signal processing unit associated with the test embodiment of FIG. 5.

The signal processing device 40 is shown in FIG. 8. The EEG conductors (2 wires) and the strain gage conductors (3 wires) were routed directly to rear-mounted banana jacks for interface to other equipment. The emitter and detector conductors were routed to the signal processing circuit via a 44 position card-edge socket. Positive and negative 12 volt power, supplied from a modular regulating power supply (Condor AA15-0.8, plus and minus 12 volts at 1 amp), also interfaces to the circuit board at this card-edge connector. The circuit board is wire-wrapped, utilizing wirewrap sockets, headers and posts for integrated circuits and components.

Figure 9:
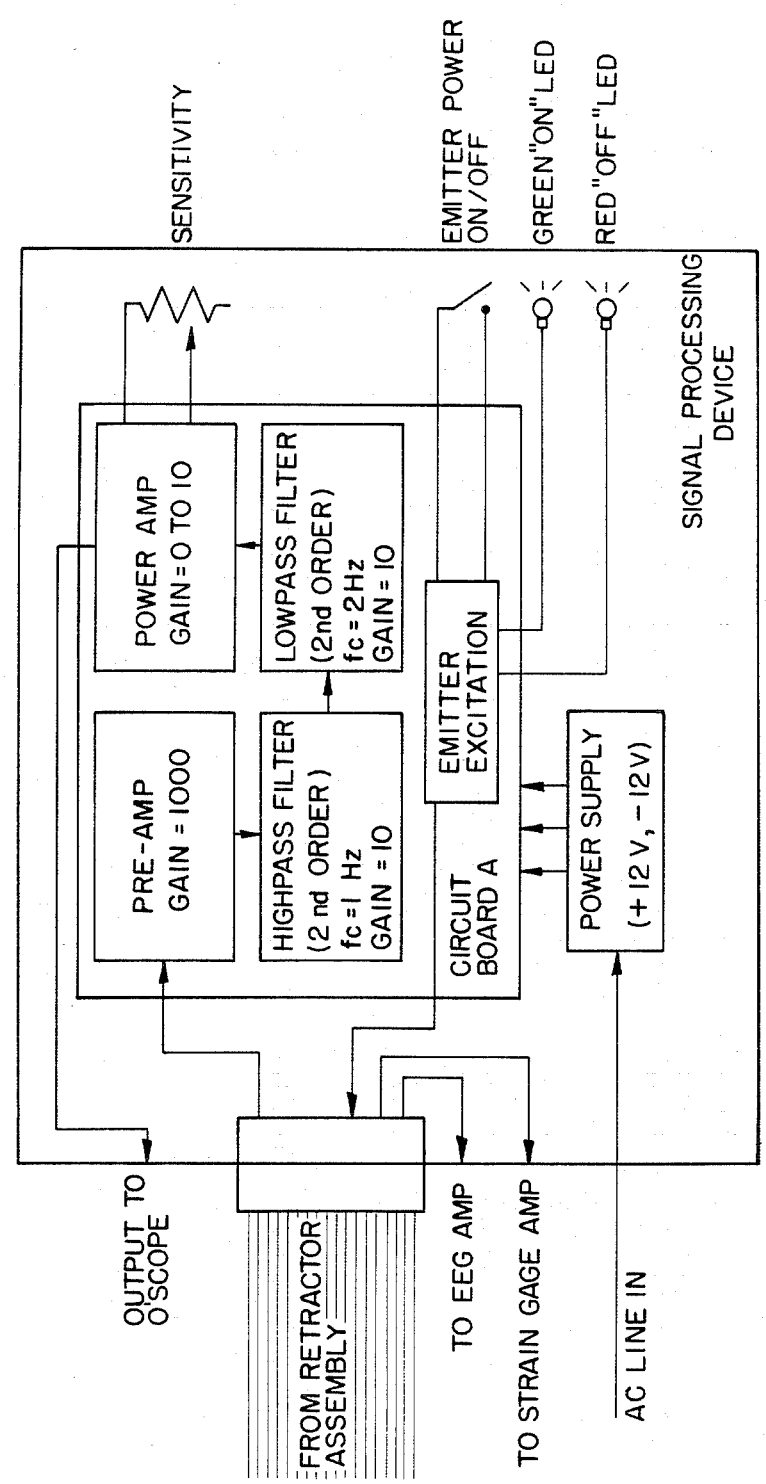
FIG. 9 is a block diagram of the signal processing unit of FIG. 8.

A signal processing circuit board was designed and tested successfully, and uses single-ended amplification, second-order filters. A block diagram of the signal processing circuit is shown in FIG. 9.

Figure 10:
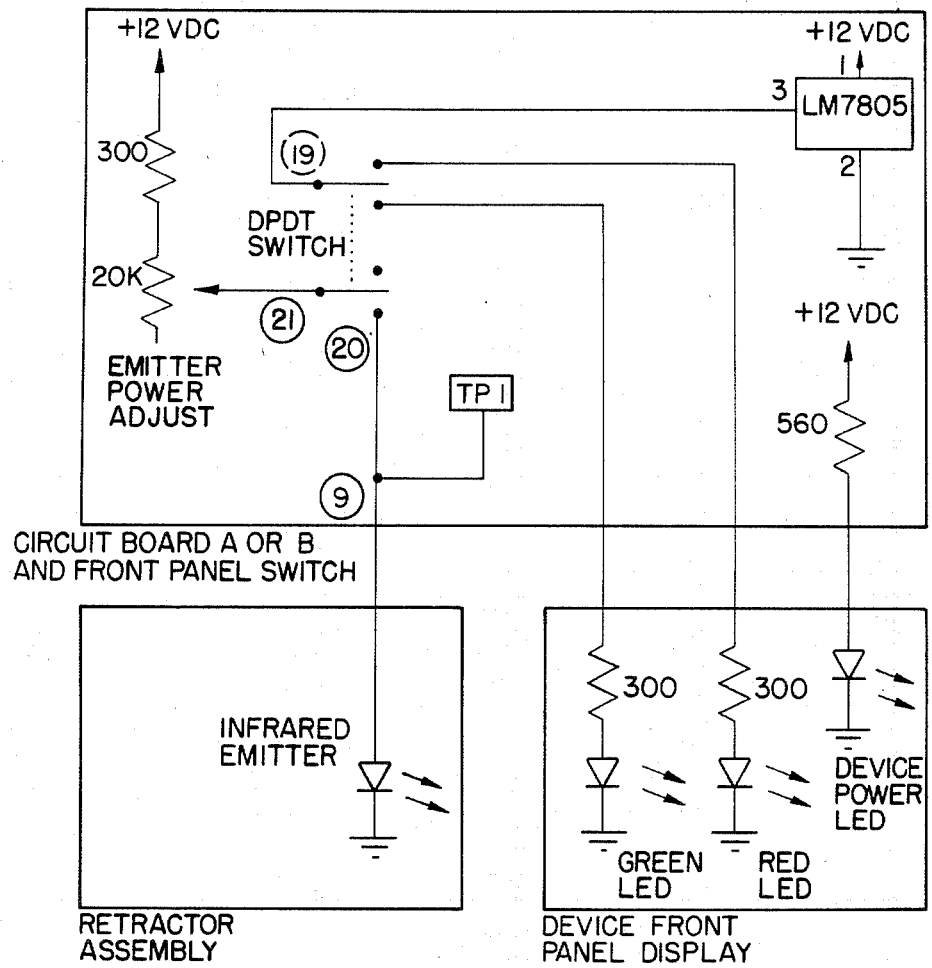
FIG. 10 is a schematic diagram of the emitter excitation circuit and device power indicator.

FIG. 10 illustrates a schematic diagram of the emitter excitation circuit and power indicator circuit. The infrared photodiode emitter current is adjusted with a board-mounted 20K potentiometer. A 300 ohm current protection resistor limits this current to 40 mA of continuous forward current. A double-pole, double-throw (DPDT), panel-mounted switch is used to connect or disconnect the infrared emitter from its excitation voltage.

The other pole of the DPDT switch is used to light a red or green panel-mounted LED as an indicator of the on or off state of the emitter. The green LED signifies that the emitter is on, and the red signifies that the emitter is off.

Figure 11:
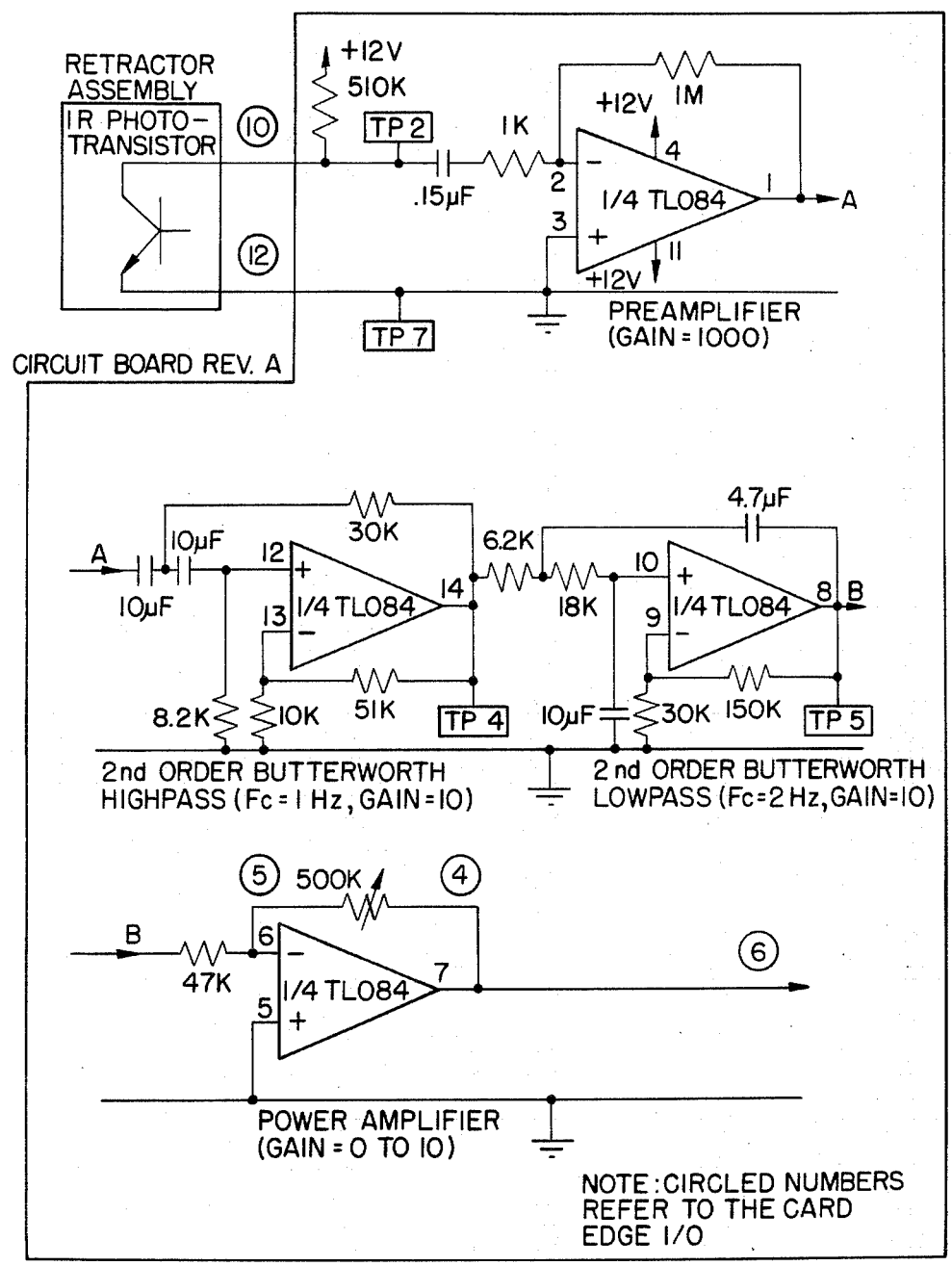
FIG. 11 is an electrical schematic diagram of the detector signal processing circuit of the unit of FIG. 8.

Signal processing for the detector signal processing circuit was accomplished with a single integrated circuit, the TL 084 Bi-FET Quad Operational Amplifier from Texas Instruments. A schematic diagram of this section of the circuit board is shown in FIG. 11.

The first amplifier of the circuit is used as a simple inverting preamplifier stage with a fixed gain of 1000. The signal from the infrared phototransistor detector is AC coupled to this amplifier to eliminate the DC bias offset of the transistor and to prevent saturation of the op-amp output.

The second and third amplifiers of the circuit are configured to provide bandpass filtering of the detector signal. Low frequency baseline shifts and respiration artifact can contaminate the cerebral pulsation signal, as can high frequency electromagnetic interference from electrosurgical devices and electrical machinery such as skull drills. To minimize these noise signals, the bandwidth of the filter was chosen to be 1 Hz, with a center frequency of 1.4 Hz (yielding a lower cutoff frequency of 1 Hz and an upper cutoff frequency of 2 Hz). For this filtering arrangement, the fractional bandwidth (which equals the difference in upper and lower cutoff frequencies divided by the center frequency) is 0.71. This indicates that the filter can be built by cascading separately designed highpass and lowpass sections, rather than by using a "true" bandpass topology (Lancaster, 1975). The second-order highpass and lowpass sections were designed using a Salen-Key topology. Component values were determined from published nomographs (Hilburn and Johnson, 1973 and 1975) in order to produce a Butterworth or "maximally flat" frequency response. To assure a high signal-to-noise ratio, the gain of each filter section was set to 10, providing an overall gain of 100 for the entire bandpass filter.

After filtering, the detector signal is again amplified. This "power amp" section is an inverting amplifier with gain determined by the front panel "sensitivity" control. The sensitivity control provides gain adjustment of 0 to 100. Following this power amplification stage, the processed detector signal was outputed to rear-mounted banana jacks for external display on an oscilloscope or strip chart. Alternatively, in a commercial unit the processing unit is preferably equipped with a display, such as a multisegment LED bar graph display 41 as shown in FIG. 8.

Three tests were performed to evaluate and analyze the performance of the cerebral pulse detector, which were performed on craniectomized cats.

The first test was designed to determine if the cerebral pulse detector was indeed detecting blood pulsations. With the retractor lightly contacting the brain, cerebral pulsations measured by the device, systemic blood pressure and electrocardiogram were each displayed on adjacent channels of a strip chart recorder.

Figure 14:
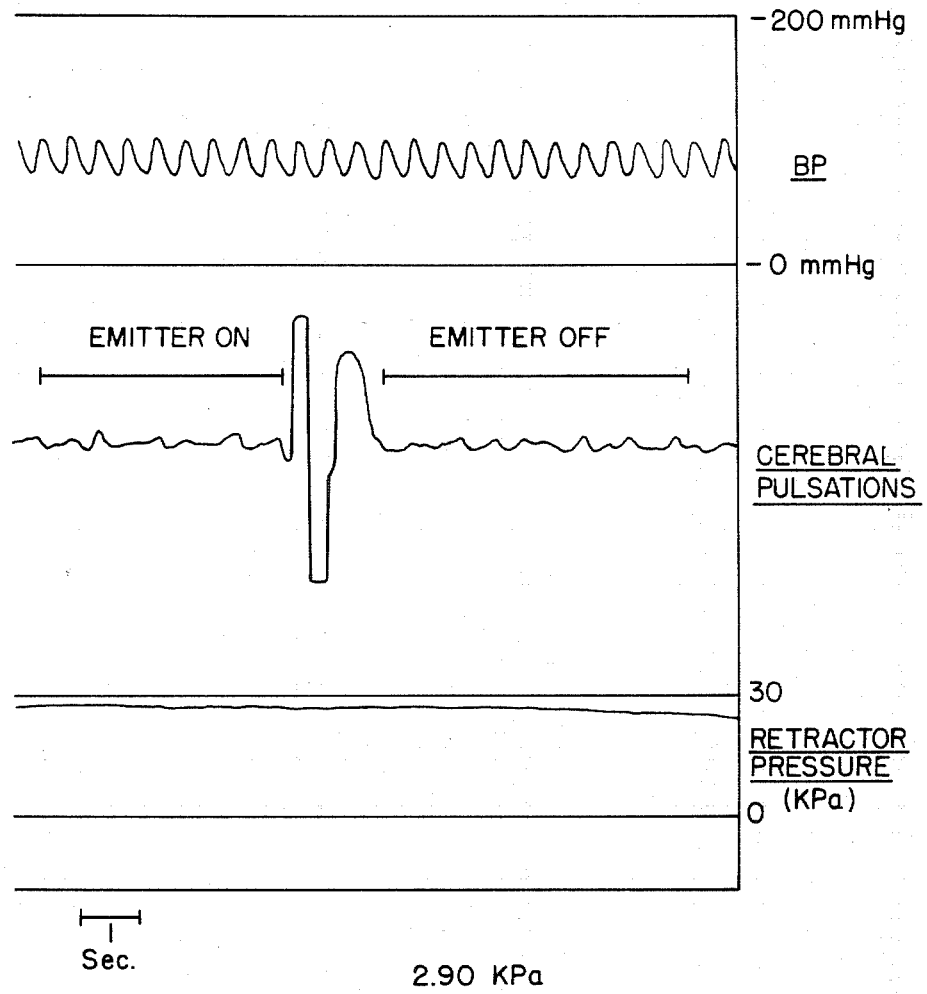

The second test involved the increase of retractor pressure on the cortical surface and the resultant changes in the cerebral pulse detector signal amplitude. Not only must the cerebral pulse detector detect blood pulsations, it must detect only from shallow vessels which will be occluded with moderate retractor pressure. To test this, the retractor was placed in a positioning device, and the retractor was then lowered to contact the brain with minimal pressure. The pulsations were recorded and their amplitude measured. Increasing pressure was applied, and the effect upon the pulsation amplitude noted. The amplitude of background pulsations (not under the retractor) could be determined at any time by turning the infrared emitter off. "Zero" pulsations were reached when the cerebral pulsation waveform remained unchanged as the infrared emitter was alternately energized and de-energized, as shown in FIG. 14.

The third test was performed to check the repeatability of the applied pressure necessary to obtain "zero" pulsations. To test this, the blood pressure was tightly regulated, and the "zero" pulsation point approached slowly and without overshoot, since any pressure over the amount needed to obtain "zero" pulsations would result in the same cerebral pulse detector signal (i.e. pulsations cannot be less than "zero," no matter how high the applied pressure) After achieving "zero" cerebral pulsations and noting the applied pressure, the retractor was quickly released. This process was repeated and the new applied pressure measured.

Figure 12:
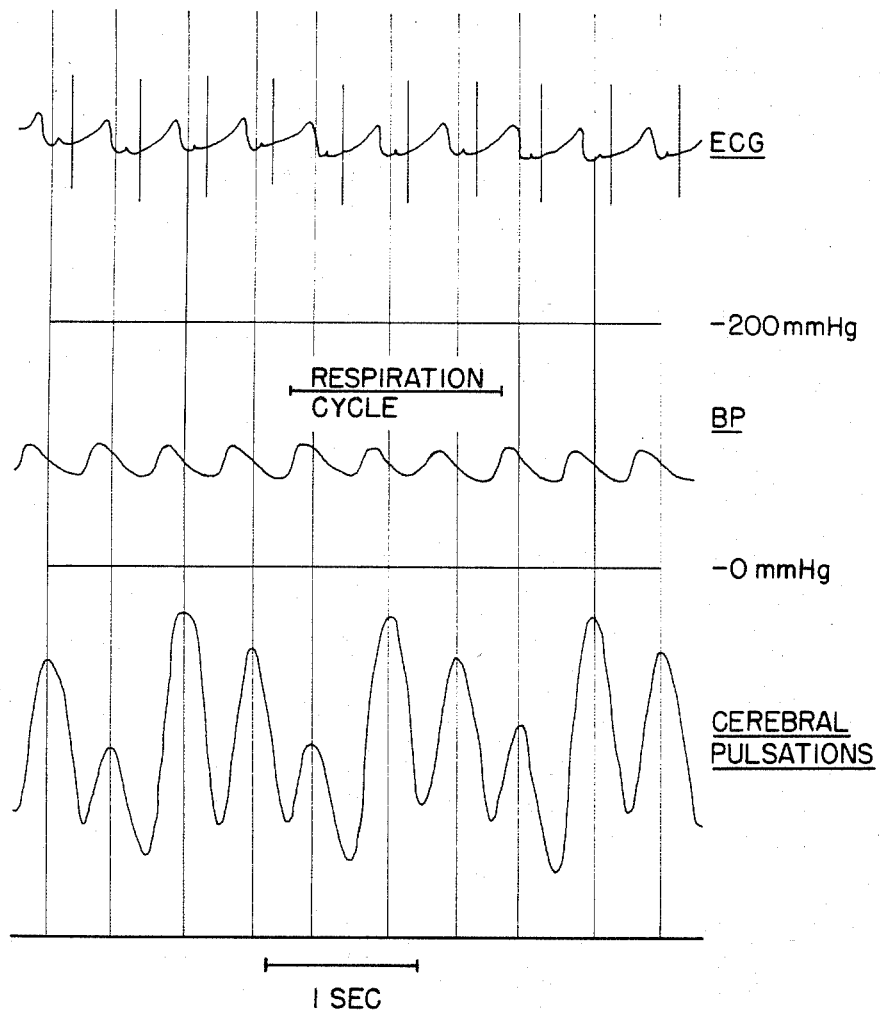
FIG. 12 is a graph of ECG signals, blood pressure signals, and cerebral pulsation signals, obtained during testing of the embodiment of FIGS. 5 and 8.
Figure 13:
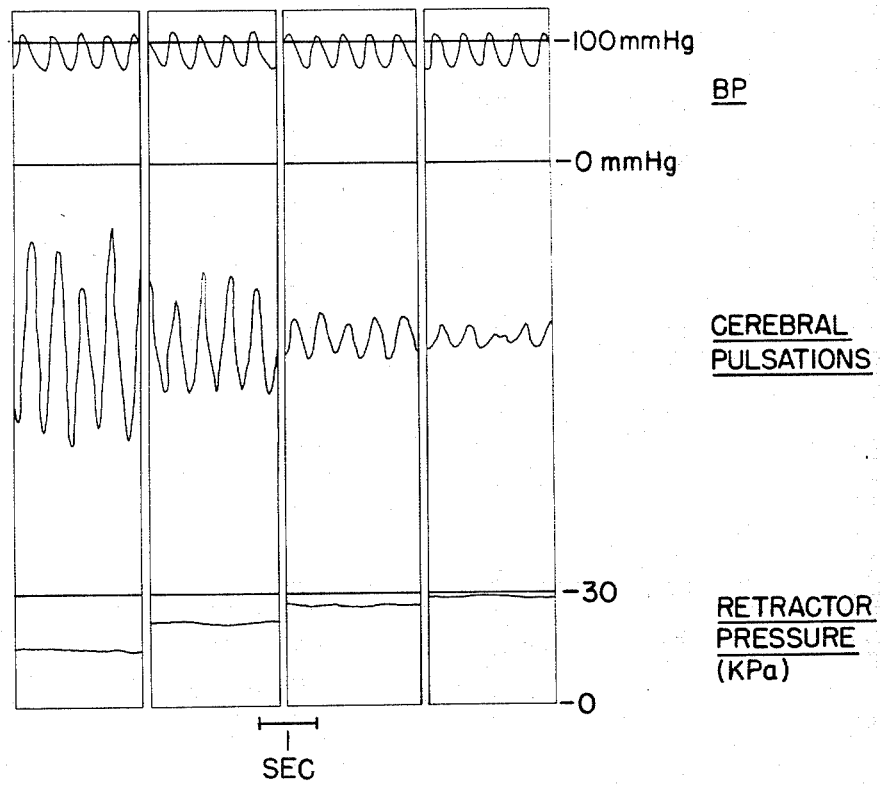
FIGS. 13 and 14 are graphs of blood pressure, cerebral pulsations, and retractor pressure signals obtained during testing of the embodiment of FIGS. 5 and 8.

Strip chart records from the three different system validation tests are shown in FIGS. 12 and 13. The first test was a check for correlation between the cerebral pulse signal and the ECG and blood pressure waveforms. The period to complete one respiration cycle is indicated in the figure and corresponds to a respirator setting of 45 breaths per minute. The second test result shows the cerebral pulsation changes as the retractor pressure is increased. The third was designed to show the repeatability of the applied pressure necessary to obtain "zero" cerebral pulsations.

Statistical correlations and significance levels were found using a SPSSX statistical software package. A least-square fit regression line, determined using SPSSX, is included in each plot. Signficance levels are found using a two-tailed Student's t-test. The null hypothesis (Ho) was that the linear correlation coefficient would be zero. The SPSSX package tested whether the actual correlation was significantly higher or lower than zero.

If the cerebral pulse detector is truly sensing cerebral blood pulsations, the pulse detector signal should show a regular series of peaks, and when compared with the ECG, the peaks should be delayed a consistent time interval from each occurrence of the QRS complex. In a like manner, cerebral pulsations and blood pressure pulsations (measured at the femoral artery) should show a regular, consistent alignment.

The results shown in FIG. 12 indicate that this correlation between signals does exist. While no formal statistics were taken to quantify the degree of correlation between traces, it is clear that ECG and blood pressure each align consistently with the cerebral pulse detector waveform. The large baseline shifts result from brain movement due to respiration. The respiration period indicated in FIG. 12 is determined by the slight rise and fall of the blood pressure waveform baseline. This same period matches the rise and fall of the pulse detector signal baseline. As the retractor is applied to the cortical surface with increasing pressure, the respiration effect has been demonstrated to be diminished substantially.

If the detector is measuring only from shallow vessels, moderate pressure should cause the cerebral pulsations to go to "zero" amplitude. If the detector is measuring too deeply, even excessive pressure which causes brain surface laceration and gross mechanical deformation of the brain will not obliterate the pulsations of the deep brain which comprises the Circle of Willis at the base of the brain will not be occluded, even with excessive pressure (Rosenorn and Diemer, 1983).

The results shown in FIG. 13 indicate that the cerebral pulsations are obliterated at moderate pressure. In this example, the applied pressure needed was 2.90 KPa. This is equivalent to 21.8 mmHg, which is consistent with the pressures reported by others as being the threshold of ischemic damage (Rosenorn and Diemer, 1983).

The "zero" cerebral pulsation point showed good repeatability. "Zero" was first obtained at 2.39 KPa, and when this process was repeated, the pressure needed was 2.25 KPa. This is a difference of 6.2%.

Because of the high transparency of brain tissue to infrared light, the cerebral pulse detector proved to be rather sensitive to ambient room light changes and to movement near the retractor foot. This necessitated that the experimenter stand motionless or clear of the retractor while measurements were being recorded.

Systemic blood pressure can vary widely in neurosurgical operations, especially when hypotension is purposefully induced during surgery for aneurysm. Therefore, use of a retractor system which relies on a measurement of absolute applied pressure alone may result in ischemic damage during hypotension, if the damage threshold is determined from normotensive experiments. If the threshold is determined using "worst case" hypotensive subjects, the surgeon will be restrained from using retraction pressures which are safe in the normotensive or hypertensive patient.

A new surgical retractor has been designed which uses infrared light to detect superficial blood pulsations in brain tissue. When the retractor was applied with pressures ranging from 1.49 KPa to 3.85 KPa, these pulsations were reduced to a minimum level. This range of pressures agrees with previously reported ischemic threshold pressures (Albin, 1977, Rosenorn and Diemer, 1982, Numoto and Donaghy, 1970). Plotting power in the delta band of the EEG against the relative percent pressure exerted by the retractor during retraction yielded a higher degree of correlation ($r=0.90$, $p=0.29$) than did plotting delta band power against absolute pressure ($r=0.40$, $p=0.74$). Pressures in excess of that needed to minimize cerebral pulsations caused an increase in delta band power, a decrease in mobility and in one case, an isoelectric EEG and extensive Evans' Blue staining. Within a single animal, mean arterial blood pressure correlated strongly with the applied pressure needed to get "zero" pulsations ($r=0.82$, $p=0.01$).

In summary, a retractor instrumentation system which assesses local blood flow in the tissue under the retractor has been proven useful in preventing tissue ischemia, especially in a clinical setting, where the brain's ability to autoregulate may be compromised. After establishing the minimum acceptable blood flow rate, the system can be designed to alert the surgeon and nurse to flows which fall below this level. The retractor pressure can then be reduced until adequate local blood flow is restored, assuring perfusion of the tissues and preventing ischemic damage. The pre-established minimum acceptable flow rate would apply in all cases, regardless of conditions which might cause abnormal cerebral perfusion pressure. When the patient is undergoing induced hypotension, for instance, use of reduced retraction pressure may be necessary to assure adequate local blood flow. Less pressure could be applied with the retractor before occluding the flow and sounding the system alarm, but the "alarm level" on the device would not need to be adjusted specifically for the induced hypotension.

As illustrated schematically in FIG. 1, in commercial embodiments the infrared emitter and detector are preferably mounted inside the signal processing device and optically connected to the retractor via fiber optic cables. This provides high electrical isolation between patient and device which would augment patient safety and increase immunity from electrical noise caused by operation of electrosurgical units. The fiber optic cable could be molded into the retractor or mounted on the retractor surface. This would help maintain the thin profile of the retractor which is necessary to keep uncluttered access to the operating site. A microprocessor-based signal processing circuit could be utilized in some embodiments to automatically modulate the emitter on and off and effectively cancel the artifact problem inherent in the test embodiment.

Another specifically identified application of the teachings of the present invention is to lumbar surgery on the spinal column to remove a ruptured lumbar disc in which a surgical retractor is used to pull the nerve root.

While several embodiments and variations of the present invention for a surgical retractor and blood flow monitor are described in detail herein, it should be apparent that the disclosure and teachings of the present invention will suggest many alternative designs to those skilled in the art.

What is claimed is:

1. A surgical retractor system for manipulation of living tissues and/or organs during diagnostic and/or surgical procedures, providing for the monitoring of the presence or absence of blood flow in the tissue adjacent to the surgical retractor, comprising:
   a. a retractor blade;
   b. said retractor blade including means for directing light having predetermined spectral characteristics related to blood onto the adjacent tissues and/or organs;
   c. said retractor blade also including light receiving means mounted in cooperative relationship with said light directing means for receiving light which is reflected from the tissues and/or organs; and
   d. signal processing means coupled to said light receiving means for monitoring the signal received therefrom for indicating the presence or absence of blood flow through the adjacent tissues and/or organs.

2. A surgical retractor system as specified by claim 1, said means for directing light having predetermined spectral characteristics providing infrared radiation having the predetermined spectral characteristics.

3. A surgical retractor system as specified by claim 1, said retractor blade including at least one light supplying optical fiber extending from a remote light source at a remote end of said light supplying optical fiber to a site end thereof at the site of the adjacent tissues and/or organs to direct light from said site end onto the tissues and/or organs, and at least one light detecting optical fiber extending from a site end of said light detecting optical fiber at the site of the adjacent tissues and/or organs at which it receives light reflected from the tissues and/or. organs and directs the light to a remote end of said light detecting optical fiber at which the light is detected.

4. A surgical retractor system as specified by claim 3, further including a remote processing unit coupled to said remote end of said at least one light supplying optical fiber and having a light source to provide light into said remote end of said light supplying optical fiber, and said remote processing means including said signal processing means, which includes a light detector coupled to said remote end of said at least one light detecting optical fiber to detect the light reflected from the tissues and/or organs.

5. A surgical retractor system as specified by claim 4, said remote processing unit providing a visual display indicating the monitored status of the flow of blood through the adjacent tissues and/or organs.

6. A surgical retractor system as specified by claim 4, said remote end of the at least one light supplying optical fiber and said remote end of the at least one light detecting optical fiber being removably coupled to said remote processing unit, whereby one of several of said retractor blades may be selectively coupled to said remote processing unit.

7. A surgical retractor system as specified by claim 3, said at least one light supplying optical fiber having a beveled site end to reflect light supplied thereto onto the adjacent tissues and/or organs through a first given solid angle, and said at least one light detecting optical fiber having a beveled site end to reflect light received from the adjacent tissues and/or organs through a second given solid angle into the at least one light detecting optical fiber for detection thereof, and said first given solid angle intersecting said second given solid angle to enable light reflected from the adjacent tissues and/or organs to be detected.

* * * * *